United States Patent
Balakrishnan et al.

(10) Patent No.: US 11,862,334 B2
(45) Date of Patent: Jan. 2, 2024

(54) FLIGHT TIME

(71) Applicant: NIKE, Inc., Beaverton, OR (US)

(72) Inventors: SantoshKumar Balakrishnan, Hillsboro, OR (US); Robert M. Bruce, Portland, OR (US); Justin Fraga, Portland, OR (US); Paul J. Francis, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 103 days.

(21) Appl. No.: 17/157,577

(22) Filed: Jan. 25, 2021

(65) Prior Publication Data

US 2021/0151181 A1     May 20, 2021

Related U.S. Application Data

(63) Continuation of application No. 16/253,877, filed on Jan. 22, 2019, now Pat. No. 10,933,281, which is a
(Continued)

(51) Int. Cl.
*G16H 40/67* (2018.01)
*A63B 24/00* (2006.01)
(Continued)

(52) U.S. Cl.
CPC .............. *G16H 40/67* (2018.01); *A43B 3/34* (2022.01); *A63B 24/0021* (2013.01);
(Continued)

(58) Field of Classification Search
CPC ........ G16H 40/67; G16H 20/30; G16H 40/63; A63B 24/0021; A63B 24/0062;
(Continued)

(56) References Cited

U.S. PATENT DOCUMENTS

| 5,343,445 A | 8/1994 | Cherdak |
| 5,720,200 A | 2/1998 | Anderson et al. |

(Continued)

FOREIGN PATENT DOCUMENTS

| CN | 2117626 U | 9/1992 |
| CN | 1272926 A | 11/2000 |

(Continued)

OTHER PUBLICATIONS

Mar. 4, 2015—(WO) ISR & WO—App. No. PCT/US14/068067.
(Continued)

*Primary Examiner* — Allen Chan
(74) *Attorney, Agent, or Firm* — Banner & Witcoff, Ltd.

(57) ABSTRACT

Systems and methods for monitoring athletic performances include determining "flight time," e.g., the amount of time both feet are off the ground, and optionally "flight time" resulting from different types of activities, such as jogging, running, sprinting, jumping, etc. "Flight time" may help a player or coach better understand the effort the athlete is putting out, compare efforts of two or more players, gauge the athlete's performance change over time, and/or identify conditioning needs and/or areas for improvement. Such systems and methods also may generate and display various athletic performance metrics, such as: instantaneous flight time; average flight time; cumulative flight time during an athletic performance or other time period; instantaneous jump height; average jump height; cumulative jump height during an athletic performance or other time period; and comparisons of any flight time and/or jump height metric(s) of one player against another player and/or against himself/herself; etc.

23 Claims, 10 Drawing Sheets

Related U.S. Application Data continuation of application No. 15/877,649, filed on Jan. 23, 2018, now Pat. No. 10,207,149, which is a continuation of application No. 15/346,963, filed on Nov. 9, 2016, now Pat. No. 9,908,000, which is a continuation of application No. 14/725,806, filed on May 29, 2015, now Pat. No. 9,523,704, which is a continuation of application No. 14/558,016, filed on Dec. 2, 2014, now Pat. No. 9,529,011.

(60) Provisional application No. 61/911,420, filed on Dec. 3, 2013, provisional application No. 61/910,912, filed on Dec. 2, 2013.

(51) Int. Cl.
| | | |
|---|---|---|
| *A43B 3/34* | (2022.01) | |
| *G01P 13/00* | (2006.01) | |
| *G04G 21/00* | (2010.01) | |
| *G01P 15/00* | (2006.01) | |
| *G16H 20/30* | (2018.01) | |
| *G16H 40/63* | (2018.01) | |

(52) U.S. Cl.
CPC .......... *A63B 24/0062* (2013.01); *G01P 13/00* (2013.01); *G01P 15/00* (2013.01); *G04G 21/00* (2013.01); *G16H 20/30* (2018.01); *G16H 40/63* (2018.01); *A63B 2024/0056* (2013.01); *A63B 2220/20* (2013.01); *A63B 2220/836* (2013.01)

(58) Field of Classification Search
CPC ........ A63B 2024/0056; A63B 2220/20; A63B 2220/836; G01P 13/00; G01P 15/00; G04G 21/00; A43B 3/34
USPC .......................................................... 700/91
See application file for complete search history.

(56) References Cited

U.S. PATENT DOCUMENTS

| | | |
|---|---|---|
| 6,611,789 B1 | 8/2003 | Darley |
| 6,876,947 B1 | 4/2005 | Darley et al. |
| 8,077,915 B2 | 12/2011 | Thorn |
| 8,460,001 B1 | 6/2013 | Chuang |
| 8,860,584 B1 | 10/2014 | Matak |
| 8,990,006 B1 | 3/2015 | Wallace et al. |
| 2003/0163283 A1 | 8/2003 | O'Brien |
| 2004/0087366 A1 | 5/2004 | Shum et al. |
| 2007/0010720 A1 | 1/2007 | Mott |
| 2007/0213126 A1 | 9/2007 | Deutsch et al. |
| 2008/0171636 A1 | 7/2008 | Usui et al. |
| 2008/0258917 A1 | 10/2008 | Boyd et al. |
| 2010/0063778 A1 | 3/2010 | Schrock et al. |
| 2010/0063779 A1 | 3/2010 | Schrock et al. |
| 2010/0184564 A1 | 7/2010 | Molyneux et al. |
| 2010/0204615 A1 | 8/2010 | Kyle et al. |
| 2011/0054359 A1 | 3/2011 | Sazonov et al. |
| 2011/0282594 A1 | 11/2011 | Vock et al. |
| 2012/0015779 A1 | 1/2012 | Powch et al. |
| 2012/0029666 A1 | 2/2012 | Crowley et al. |
| 2012/0078594 A1* | 3/2012 | Jallon .................... A61B 5/112 703/2 |
| 2012/0212505 A1 | 8/2012 | Burroughs et al. |
| 2012/0234111 A1 | 9/2012 | Molyneux et al. |
| 2012/0251079 A1 | 10/2012 | Meschter et al. |
| 2013/0109762 A1 | 5/2013 | Lammel et al. |
| 2013/0190903 A1 | 7/2013 | Balakrishnan et al. |
| 2013/0213144 A1 | 8/2013 | Rice et al. |
| 2014/0195538 A1 | 7/2014 | Downs et al. |
| 2014/0288878 A1 | 9/2014 | Donaldson |
| 2015/0057966 A1 | 2/2015 | Winter et al. |

FOREIGN PATENT DOCUMENTS

| | | |
|---|---|---|
| CN | 2796774 Y | 7/2006 |
| CN | 101111743 A | 1/2008 |
| CN | 101119773 A | 2/2008 |
| CN | 101304675 A | 11/2008 |
| CN | 101367012 A | 2/2009 |
| CN | 101583403 A | 11/2009 |
| CN | 102341149 A | 2/2012 |
| CN | 102754015 A | 10/2012 |
| JP | H05122269 A | 5/1993 |
| JP | H09122269 A | 5/1997 |
| JP | 2013220356 A | 10/2013 |
| JP | 6246370 B2 | 12/2017 |
| KR | 20130095326 A | 8/2013 |
| KR | 20130096310 A | 8/2013 |
| WO | 2004089213 A1 | 10/2004 |
| WO | 2010096691 A2 | 8/2010 |
| WO | 2012064956 A1 | 5/2012 |
| WO | 2012161768 A1 | 11/2012 |
| WO | 2013022344 A1 | 2/2013 |
| WO | 2013109762 A1 | 7/2013 |

OTHER PUBLICATIONS

Feb. 26, 2015—(WO) ISR & WO—App. No. PCT/US14/068149.
Andrea Mannini, et al., "Machine Learning Methods for Classifying Human Physical Activity from On-Body Accelerometers," Feb. 1, 2010; Open Access Sensors, Sensors 2010, pp. 1154-1175.

* cited by examiner

FLIGHT TIME

CROSS-REFERENCE TO RELATED APPLICATIONS

This application is a continuation of and claims priority to Ser. No. 16/253,877 filed Jan. 22, 2019, which is a continuation of and claims priority to U.S. patent application Ser. No. 15/877,649 filed Jan. 23, 2018, now U.S. Pat. No. 10,207,149 issued Feb. 19, 2019, which is a continuation of and claims to priority to U.S. patent application Ser. No. 15/346,963 filed Nov. 9, 2016, now U.S. Pat. No. 9,908,000 issued Mar. 6, 2018, which claims the benefit of and priority to U.S. patent application Ser. No. 14/725,806 filed May 29, 2015, now U.S. Pat. No. 9,523,704 issued Dec. 20, 2016, which claims the benefit of and priority to U.S. patent application Ser. No. 14/558,016 filed Dec. 2, 2014, now U.S. Pat. No. 9,529,011 issued Dec. 27, 2016, which claims the benefit of and priority to U.S. Provisional Patent Application No. 61/911,420 filed Dec. 3, 2013 and U.S. Provisional Patent Application No. 61/910,912 filed Dec. 2, 2013, which are expressly incorporated herein by reference in their entireties for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities also may be too focused on one or more particular activities while an individual's interests are ignored. This may further decrease a user's interest in participating in athletic activities or using athletic activity services and systems.

Further, with regard to professional and/or serious amateur athletes (e.g., pro-am athletes), many existing services and devices fail to provide accurate assessment of one or more metrics, such as their performance, performance load, reaction, fatigue, among others. Existing devices for flight time monitoring often suffer from one or more deficiencies, including: cumbersome collection systems, inaccurate measurements that are beyond an acceptable threshold, unacceptable latency in reporting the values, erroneous classification of activities based upon detected motions of the user, failure to account for deviations between different users, inapplicability of the collected or processed data to measure performance or other metrics, relatively high power consumption, and/or a combination of these or other deficiencies.

Specific to airtime or flight time, prior attempts attempting to incorporate airtime as a metric merely focused on flight of one or both feet in the context of jumps. For example, with reference to basketball players, prior attempts may have considered an offensive player making a jump shot or a defensive player attempting to jump up to block the shot of the offensive player to determine flight time. As would therefore be expected, such results would be highly correlated to total jumps during the same time period.

Therefore, improved systems and methods to address at least one or more of these shortcomings in the art are desired.

SUMMARY

One or more of the deficiencies above and/or other shortcomings of existing solutions may be overcome by one or more aspects of the innovations described herein. In accordance with one embodiment, a sensor system integrated directly into footwear, including but not limited to that typically worn by athletes for most activities. Embodiments relate to measuring and tracking one or more athletic metrics including, but not limited to, flight time.

Aspects of this invention relate to systems and methods for monitoring athletic performances, as well as to non-transitory computer-readable media that include computer-executable instructions stored thereon for performing the methods, running the systems, and/or providing the output data and displays to a user. In some aspects of this invention, athletic performances will be monitored to determine "flight time," e.g., the amount of time when both of the athlete's feet are not in contact with a ground surface, and optionally "flight time" as a result of various different types of athletic activities, such as jogging, running, sprinting, jumping, or the like. "Flight time" may represent and/or help a player or coach better understand the amount of effort the athlete is putting out, better compare the efforts of two or more players, better gauge the athlete's performance change over time, and/or better identify conditioning needs and/or areas for improvement. Systems and methods according to at least some aspects of this invention also may generate and display various athletic performance metrics, such as: instantaneous flight time (e.g., milliseconds per flight or average milliseconds/flight); average flight time (milliseconds of flight/sec); cumulative flight time over the course of an athletic performance or other time period (e.g., adding up flight time); instantaneous jump height (e.g., inches per flight); average jump height; cumulative jump height over the course of an athletic performance or other time period (e.g., adding up jump heights); comparison of any flight time and/or jump height metric(s) of one player against another player; comparison of any flight time and/or jump height metric(s) of one player against himself/herself; etc.

Some aspects of this invention relate to systems and methods for analyzing athletic performance, e.g., for determining an athlete's "flight time" and/or "jump height" during such activities. Such systems and methods may include a computer system for receiving input data, processing that data, and outputting data including athletic performance analysis information and/or metrics in a human perceptible manner. Such systems and methods may include input systems that: (a) receive right foot launch input data from a right foot sensor system relating to a plurality of right foot launch events, wherein the right foot launch input data includes at least a timestamp associated with each right foot launch event indicating a time that respective right foot launch event occurred; (b) receive left foot launch input data from a left foot sensor system relating to a plurality of left foot launch events, wherein the left foot launch input data includes at least a timestamp associated with each left foot launch event indicating a time that respective left foot launch event occurred; (c) receive right foot strike input data from a right foot sensor system (e.g., the same or a different sensor system) relating to a plurality of right foot strike events, wherein the right foot strike input data includes at least a timestamp associated with each right foot strike event indicating a time that respective right foot strike event occurred; and (d) receive left foot strike input data from a left foot sensor system (e.g., the same or a different sensor system) relating to a plurality of left foot strike events, wherein the left foot strike input data includes at least a timestamp associated with each left foot strike event indicating a time that respective left foot strike event occurred. From this input information, a computer processing system (e.g., including one or more micro-processors or other computer components) may identify a first set of timestamps (or plural sets of timestamps), wherein the first set of timestamps (and optionally each set of timestamps) includes temporally adjacent right foot launch, left foot launch, right foot strike, and left foot strike events. A first flight time for the first set of timestamps (and optionally flight times for at least some, and optionally each of the sets of timestamps) then may be determined based at least in part on a time duration included by the first set of timestamps when both the left foot and the right foot are simultaneously not in contact with a ground surface. As will be discussed in more detail below, systems and methods according to at least some aspects of this invention will evaluate the determined flight time(s) to determine if they are potentially invalid and, if so, in at least some instances, correct the potentially invalid data or discard that data. Systems and methods according to at least some examples of this invention also will include generating output, e.g., including information relating to or based on one or more of the metrics described above, and transmitting the output data and/or generating a user interface displaying at least some of the output/metrics in a human perceptible manner.

Other example systems and methods according to this aspect of the invention may include: (a) a right foot sensor for measuring acceleration of a right shoe or contact force between a right shoe and a contact surface; (b) a left foot sensor for measuring acceleration of a left shoe or contact force between a left shoe and a contact surface; (c) a processor system programmed and adapted to: (i) identify right foot launch events, left foot launch events, right foot strike events, and left foot strike events from data generated by the right foot sensor and the left foot sensor; (ii) identify a plurality of sets of event timestamps, wherein the sets of event timestamps include temporally adjacent right foot launch, left foot launch, right foot strike, and left foot strike events; and (iii) determine flight times associated with at least some of the plurality of sets of event timestamps, wherein each flight time is based at least in part on a time duration included by a corresponding set of timestamps when both the left foot and the right foot are simultaneously not in contact with a surface; and (d) an output system for outputting output data including information containing or derived from the flight times.

Systems and methods according to at least some aspects of this invention may include any, some, or all of the features or characteristics described below.

Systems and methods according to at least some aspects of this invention further will include right foot sensor systems and left foot sensor systems, e.g., for sensing, measuring, and detecting one or more of: acceleration; changes in acceleration; velocity of movement; changes in velocity; position; changes in position; contact force between a foot and a contact surface; changes in contact force between the foot and a contact surface; etc.

In the step of determining the flight time for a set of timestamps, the flight time may be determined using the following equation:

$$\text{Flight Time} = T1 - T2,$$

wherein T1 corresponds to a time of a timestamp from the set of timestamps associated with an earlier of the right foot strike event or the left foot strike event and T2 corresponds to a time of a timestamp from the set of timestamps associated with a later of the right foot launch event or the left foot launch event. To correspond to walking, jogging, running, or sprinting activities, the last foot to leave the ground (corresponding to the T2 timestamp event) will be the opposite foot from that to first contact the ground (corresponding to the T1 time event). For jumping activities (and potentially both vertical jumping and running jumps), the feet may leave the ground and contact the ground in any order.

In at least some examples of systems and methods according to this invention, in the step of determining the flight time for a set of timestamps: (a) the flight time associated with a set of timestamps will be determined to be 0 if the timestamp associated with T1 is earlier than the timestamp associated with T2; and/or (b) the flight time associated with a set of timestamps will be determined to be 0 if the determined flight time value is less than a threshold time duration (e.g., a short but positive "flight time" that may correspond essentially to walking activity, optionally walking with a little "bounce" in one's step).

At least some examples of systems and methods according to this invention will evaluate determined flight times for a set of timestamps to determine whether the flight time is "valid" for human activity. As one example, in the step of determining the flight time for a set of timestamps, the flight time associated with a set of timestamps may be determined to be 0 if the determined flight time value is greater than a valid flight time value (e.g., an upper threshold time limit set greater than possible for an individual to lose contact with the ground by jumping without some external assistance to suspend or support him/her). The "valid flight time value" may be set at a value for people in general (e.g., corresponding to a time period near and/or just greater than a highest jump time ever recorded) or it may be set at a level targeted to an individual's previously determined abilities.

A determination that a determined flight time value exceeds a valid flight time value does not automatically require a determination of a 0 flight time for that set of timestamps in all systems and methods according to this invention. Rather, if desired, systems and methods according to at least some examples of this invention may consider data from other sources, such as other sensors (e.g., a body core sensor, a video data stream, etc.), to determine whether a determined invalid flight time value can be "corrected." For example, in basketball, sometimes a player will grasp the net or rim or will be held up by another player and be "suspended" in the air for a time, which may cause the determined flight time value to exceed a "valid flight time value." To handle such events (e.g., when the flight time value exceeds the valid flight time value) and in an effort to provide more accurate "flight time" data, systems and methods according to at least some examples of this invention may receive input data from a motion sensor system other than the right foot sensor and the left foot sensor system (e.g., a body core motion sensor or accelerometer, etc.), and using that data (and timestamp information associated with it) along with the set of timestamp data being evaluated, see if a "suspension time" can be determined from the motion sensor/accelerometer input data between: (i) a time of a timestamp associated with an earlier of the right foot strike event or the left foot strike event and (ii) a time of a timestamp associated with a later of the right foot launch event or the left foot launch event. If a suspension time can be determined (e.g., when the body core sensor or accelerometer shows the player to maintain an elevated height for an extended time period that defies gravity), systems and methods according to this aspect of the invention may: determine if a "corrected" time duration (e.g., corresponding to the initially determined flight time value minus the suspension time) is less than a second valid flight time value (which may be the same as or different from the initial valid flight time value used above) and (A) if so, determine the flight time for that set of timestamps based, at least in part, on the "corrected" time duration (e.g., equal to the "corrected time duration"), and (B) if not, determine the flight time for that set of timestamps to be 0. If desired, some systems and methods may determine if a "suspension time" can be found associated with any set of timestamps, even timestamps that result in a valid determined flight time, and use the "suspension time," when present, to correct even valid flight time values.

As another example, a determined flight time value could exceed a valid flight time value when a player does not land on his/her feet after a step or jump (and thus, the next "foot strike" event may not occur until the player starts to gets up, which may extend the time period longer than the valid flight time value). If a player is knocked down during play, they still should get credit for "flight time" associated with their activities, but that flight time should not be skewed to include the time it takes to stand up. Systems and methods according to at least some examples of this invention also may determine and "correct" the flight time in at least some of these instances. Again, systems and methods according to at least some examples of this invention may consider data from other sources, such as other sensors (e.g., a body core sensor, a video data stream, etc.), to determine whether a player did not land on his/her feet and whether a determined invalid flight time value can be "corrected." More specifically, if the flight time associated with a set of timestamps is determined to be greater than a first valid flight time value, systems and methods according to at least some examples of this invention further may include: determining if a ground contact time can be determined from the other sensor data (e.g., an abrupt change in acceleration from a body core accelerometer sensor) between: (a) a time of a timestamp associated with an earlier of the right foot strike event or the left foot strike event and (b) a time of a timestamp associated with a later of the right foot launch event or the left foot launch event. If a potential ground contact time can be determined from this other data, the systems and methods may further: determine if a second time duration between the ground contact time from the other sensor data and the time of the timestamp associated with the later of the right foot launch event or the left foot launch event is less than a second valid flight time value (which may be the same as or different from the first valid flight time value) and (A) if so, determine the flight time for that set of timestamps based on (e.g., corresponding to) the second time duration and (B) if not, determine the flight time for that set of timestamps to be 0.

As described above, "flight times" may be determined for one or more "sets" of timestamp data, and these "sets" of timestamp data may include at least a set of four temporally adjacent right foot strike, left foot strike, right foot launch, and left foot launch events. Alternatively, the events of a set need not be temporally adjacent and/or limited to the four noted events, but the right and left foot events of a set of timestamp data may constitute all right and left foot launch and strike events that occur within a desired timeframe.

Additional aspects of this invention may involve determining "jump height" associated with one or more individual "flight time" events and/or a cumulative "jump height" associated with a plurality of "flight time" events. While other algorithms and equations can be used for determining jump height based on a determined "flight time," in at least some examples of systems and methods according to this invention, the "jump height" associated with flight time data will be determined from the equation:

$$\text{Jump Height (inches)} = (41.66708 \times \text{Flight Time (seconds)}) - 3.818335.$$

Jump height can be determined for each individual flight time and/or each individual set of timestamp data. Additionally or alternatively, a "cumulative jump height" can be determined, e.g., based on the cumulative flight time (e.g., using the equation above) or by adding the individually determined jump heights (e.g., using the equation above) for the individual flight times.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
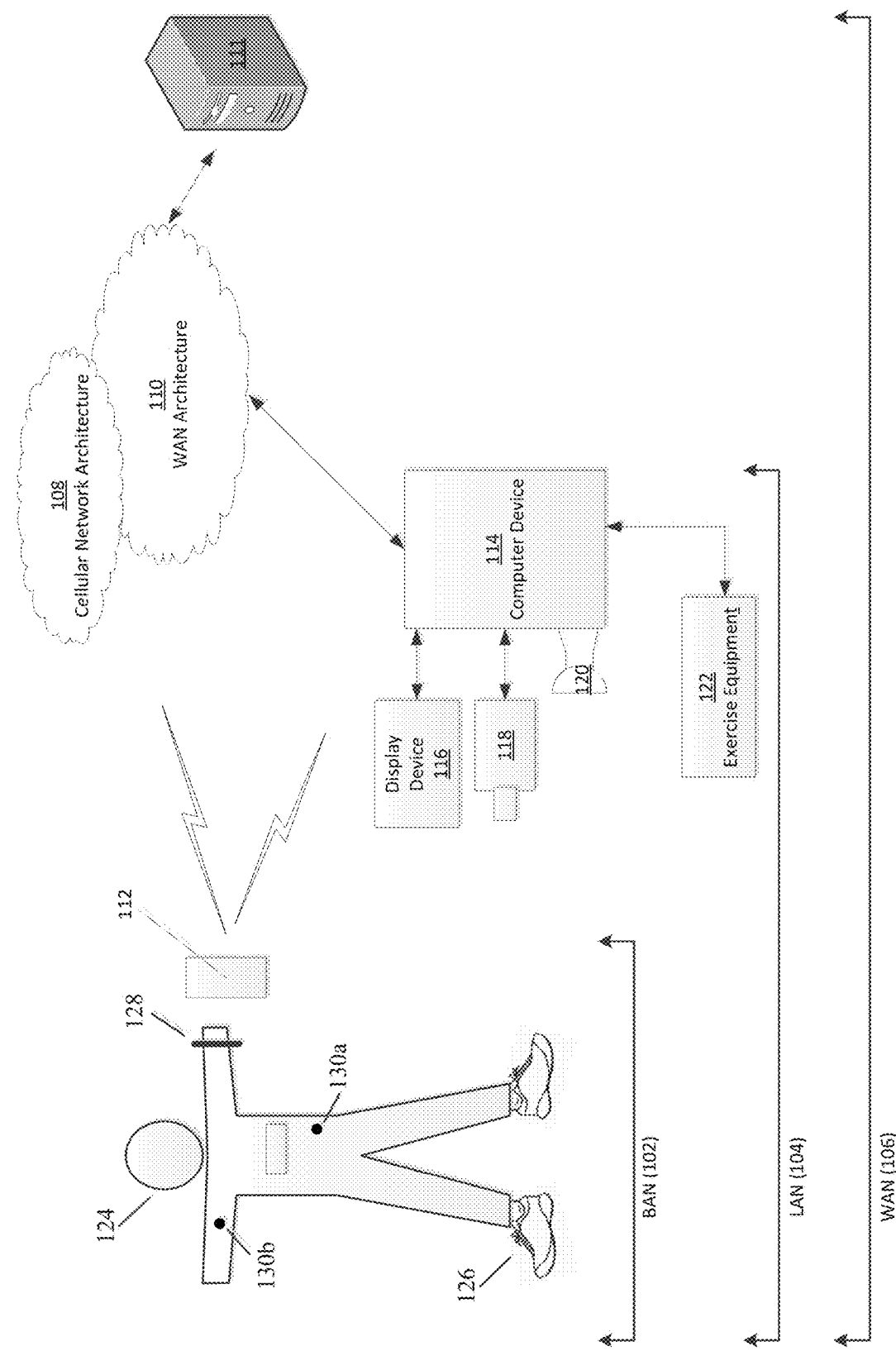
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106) may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP), through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc., and as such, may be variously configured such as having one or more wired or wireless communication channels (including but not limited to: WiFi®, Bluetooth®, Near-Field Communication (NFC) and/or ANT technologies). Thus, any device within a network of FIG. 1 (such as portable electronic device 112 or any other device described herein) may be considered inclusive to one or more of the different logical networks 102-106. With the foregoing in mind, example components of an illustrative BAN 102 and LAN 104 (which may be coupled to WAN 106) will be described.

1. Example Local Area Network

LAN 104 may include one or more electronic devices, such as computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art, given benefit of this disclosure, will appreciate that these are merely example devices for descriptive purposes and this disclosure is not limited to any console or computing device.

Figure 2:
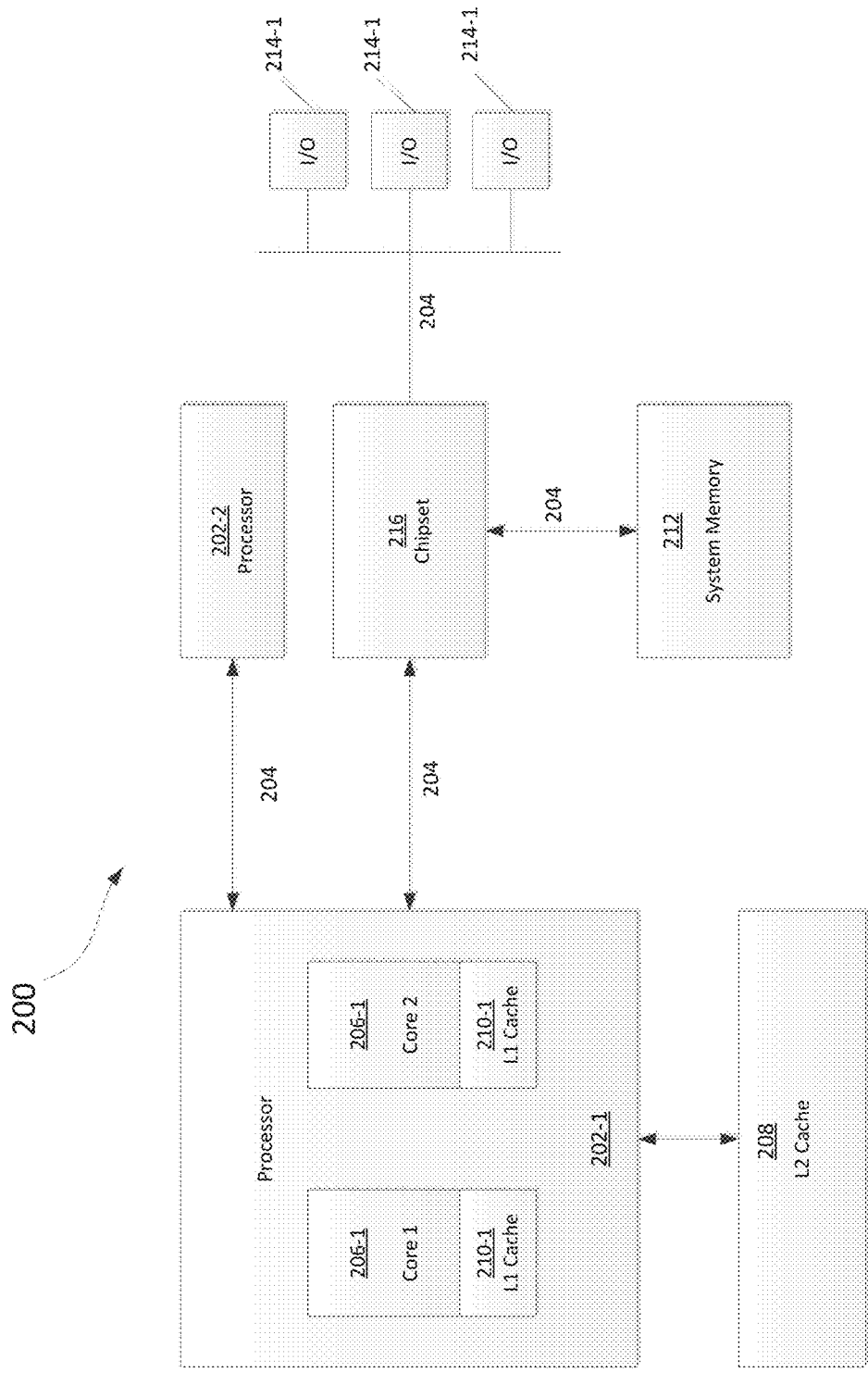
FIG. 2 illustrates an example computer device that may be part of or in communication with the system of FIG. 1.

Those skilled in the art, given benefit of this disclosure, will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 (referred to herein as "cores 206" or more generally as "core 206"), which may be implemented on a single integrated circuit (IC) chip.

Cores 206 may comprise a shared cache 208 and/or a private cache (e.g., caches 210-1). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and may include one or more of solid-state memory, optical or magnetic storage, and/or any other medium that can be used to store electronic information. Yet other embodiments may omit system memory 212.

System 200 may include one or more I/O devices (e.g., I/O devices 214-1, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to, athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), a light (including non-visible light) sensor, a temperature sensor (including ambient temperature and/or body temperature), sleep pattern sensors, a heart rate monitor, an image-capturing sensor, a moisture sensor, a force sensor, a compass, an angular rate sensor, and/or combinations thereof, among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate, given benefit of this disclosure, that such discussions are merely descriptive of some of the many options within the scope of this disclosure. Further, reference to any data acquisition unit, I/O device, or sensor is to be interpreted as disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof; physiological parameters, such as calories, heart rate, sweat detection, effort, oxygen consumed, and oxygen kinetics; and other metrics that may fall within one or more categories, such as: pressure, impact forces, information regarding the athlete, such as height, weight, age, and demographic information; and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as flight time, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120, and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN 106. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including toward the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as a treadmill, a step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that, for example, includes a telephone or digital music player, including an IPOD®, IPAD®, or iPhone®, brand devices available from Apple, Inc. of Cupertino, California or Zune® or Microsoft® Windows devices available from Microsoft of Redmond, Washington. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
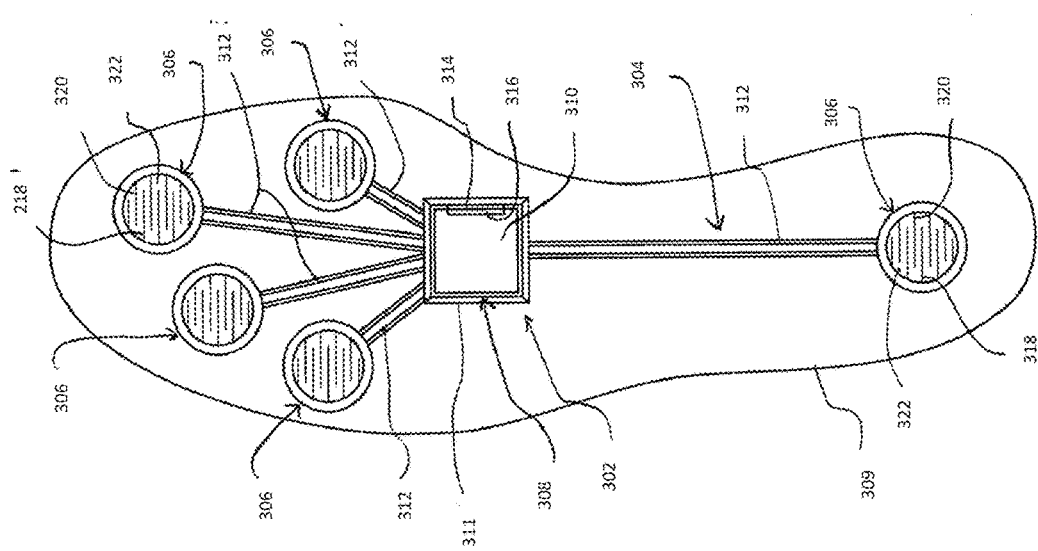
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as an accelerometer, a gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 optionally may be provided to be in communication with an electronic module 310, and the sole structure 309 optionally may include a housing 311 or other structure to receive the module 310. The sensor system 302 also may include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
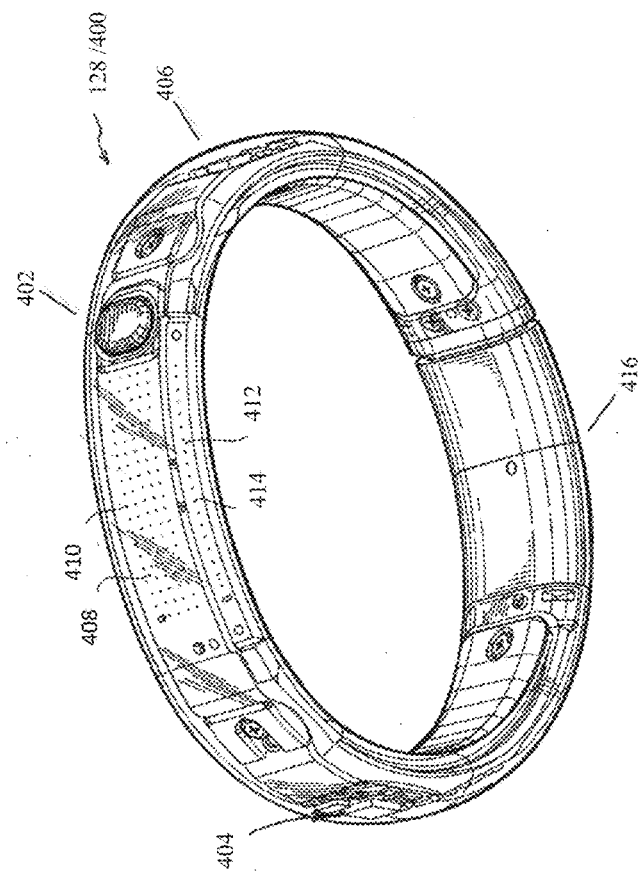
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display 408 may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
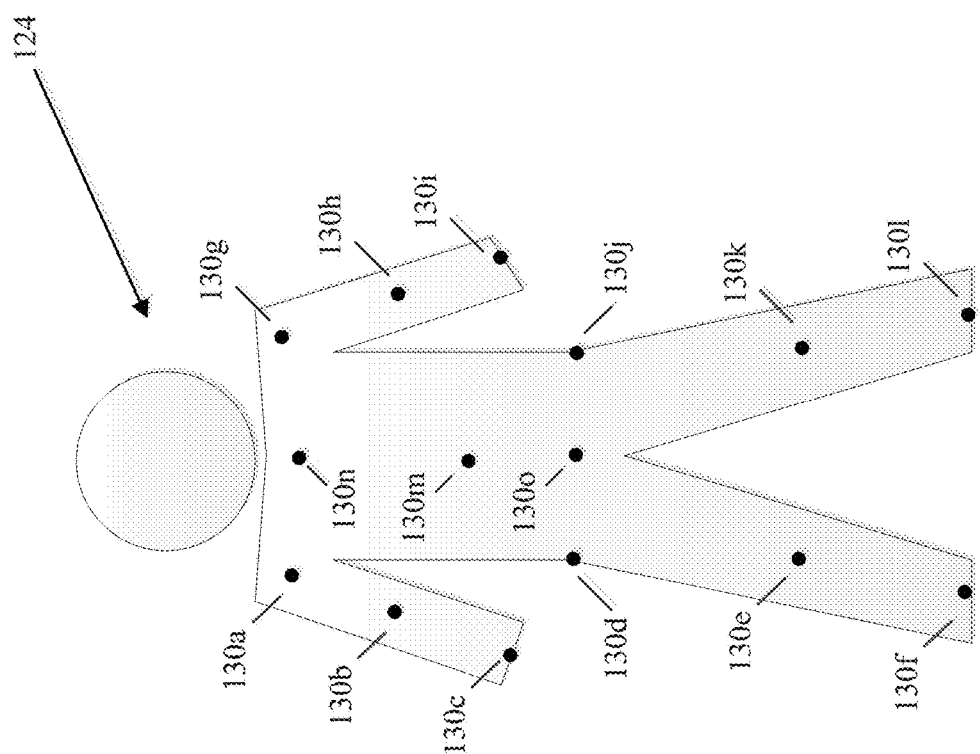
FIG. 5 shows illustrative locations for sensory input that may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 130n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

Example Metrics Calculations

Aspects of this disclosure relate to systems and methods that may be utilized to calculate one or more activity metrics of an athlete, including but not limited to steps, flight time, speed, distance, pace, power, and/or others. The calculations may be performed in real time, such that the user may obtain real-time feedback during one or more activities. In certain embodiments, all calculations for a plurality of metrics may be estimated using a same set of attributes, or a sub-set of attributes from a common group of attributes, and the like. In one embodiment, a calculation of flight time may be performed on a first set of attributes and with or without classifying the activity being performed by the athlete, such as being walking, running, playing a specific sport, or conducting a specific activity. In one embodiment, determinations of flight time may be performed with or without any activity type templates, such that as the flight time may be calculated from sensor data and/or derivatives thereof, without classifying the activity type. For example, flight time may be calculated in accordance with certain embodiments using the same set of attributes regardless of whether the athlete is performing a first activity or a second activity, such as for example, walking or playing soccer or basketball.

In certain implementations, calculations of flight time may be performed using a first set of attributes and another metric, such as jump height and/or speed, may be determined from the same set of attributes or a subset of the same attributes. In one embodiment, determination of a plurality of metrics may be conducted using a selection of core attributes. In one example, this attribute calculation may be used to estimate flight time and/or a jump height and/or speed of the user. In one more specific example, a flight time and/or speed may be estimated using a same set of attributes, or a sub-set of attributes from a common group of attributes, and the like.

The systems and methods described herein may compare calculated attributes from activity data (real-time activity data, and the like) to one or more models wherein the one or more models may not include data captured for the activity type that the athlete performed (and may not be categorized, such as for flight time calculations). In this way, the one or more models may be agnostic to the specific activity being performed by a user. For example, an activity device may receive information from a user performing a basketball activity and at least one model may not contain any data from basketball activities.

As an example of calculating multiple metrics, systems and methods may be implemented to determine whether to calculate speed for one or more time windows of data. Certain aspects of this disclosure relate to determinations of speed or distance that comprises categorizing athletic data. As discussed above, however, other aspects relate to calculating flight time values without categorizing the athletic data into activity types (walking, running, basketball, sprinting, soccer, football, etc.), however, categorizing at least a portion of the same data utilized to calculate flight time for the calculation of other metrics, such as for example, speed and/or distance is within the scope of this disclosure. In one implementation, speed (or another metric) may be determined from at least a portion of data derived from the determination of flight time values. In accordance with certain embodiments, the attributes are calculated on a single device, such as any device disclosed herein or known in the art. In one embodiment, the attributes and calculation of the metrics are calculated on a single device. In one such example, a device configured to be worn on an appendage of a user may be configured to receive sensor data and calculate the attributes and a plurality of metrics from the attributes. In one embodiment, the single device comprises at least one sensor configured capture data utilized to calculate at least one attribute. In accordance with certain embodiments, the attributes are calculated from one or more sensors located on the single device.

Example Calculations

Figure 6:
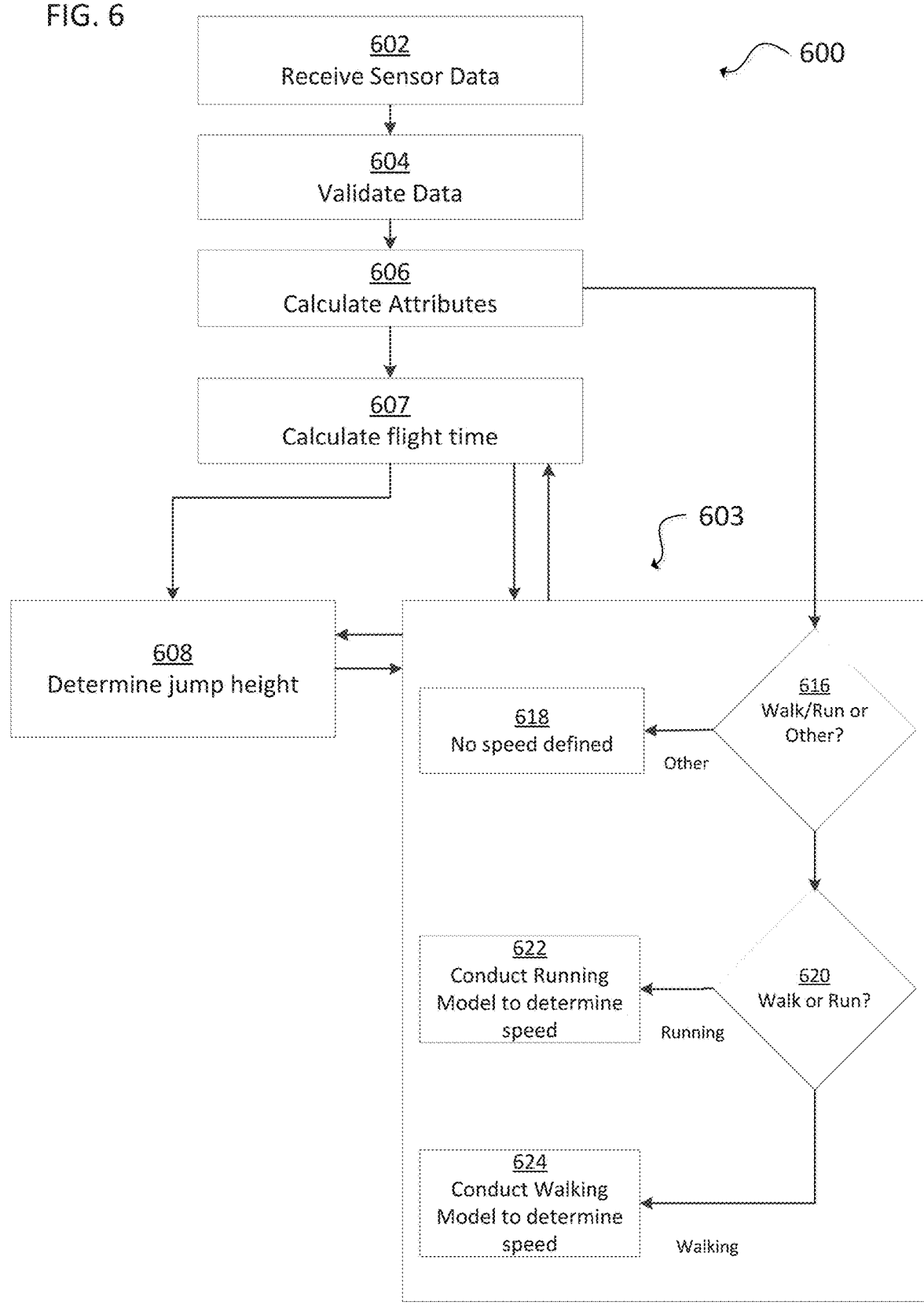
FIG. 6 shows an example flowchart that may be implemented to compute metrics, including flight time.

One or more of the systems and methods described herein may calculate an estimate of flight time that implements at least one of the components of FIG. 6. In one configuration, a device, such as device 112, 126, 128, 130, and/or 400 may capture data associated with one or more activities being performed by a user, and may include one or more sensors, including, but not limited to: an accelerometer, a gyroscope, a location-determining device (e.g., GPS), a light sensor, a temperature sensor (including ambient temperature and/or body temperature), a heart rate monitor, an image-capturing sensor, a moisture sensor and/or combinations thereof. This captured activity data may, in turn, be used to calculate one or more flight time values associated with the user.

In another example, the systems and methods described herein may be implemented to estimate one or more metrics from sensor data. These metrics may include, among others, an estimation of flight time, an estimation as to whether a user is running, walking, or performing other activity, and/or an estimation of a speed and a distance (a pace) which a user is moving, and the like. For example, block 607 of flowchart 600 from FIG. 6 shows an example implementation of calculating flight time from one or more attributes. Separately, block 603 is directed to an example implementation for calculating speed, which may be determined using one or more calculated attributes, which may be derived from the same sensors, from the same data, and/or the same attributes as the flight time metric.

Accordingly, the systems and methods described herein may utilize data received from one or more different sensor types, including, among others, an accelerometer, a heart rate sensor, a gyroscope, a location-determining device (e.g., GPS), a light (including non-visible light) sensor, a temperature sensor (including ambient temperature and/or body temperature), sleep pattern sensors, an image-capturing sensor, a moisture sensor, a force sensor, a compass, an angular rate sensor, and/or combinations thereof.

Furthermore, while the example of attributes associated with acceleration data output from an accelerometer sensor are described, those of ordinary skill will appreciate, given benefit of this disclosure, that other sensors may be used, alone or in combination with other sensors and devices, without departing from the scope of this disclosure. For example, a heart rate monitor may be used, wherein the data output from a heart rate monitor may output data representative of a heart rate in units of beats per minute (BPM) or equivalent. Accordingly, one or more transformations may be performed on outputted heart rate data to interpolate a heart rate signal between heart rate data points, and allowing for signal dropouts at certain points. Furthermore, the attributes calculated for sensor data associated with a heart rate monitor, or any other sensor, may be the same, or may be different to those described above in relation to accelerometer data.

In another implementation, the systems and methods described herein may analyze sensor data from combinations of sensors. For example, a device may receive information related to motion of two or more appendages of a user (from one or more accelerometers, and the like). In one example, the device may determine that accelerometer data may indicate that said user could not have been "in-flight" above a certain time period.

In certain embodiments, all sensor data comes from a unitary device. In one example, the unitary device is an appendage-worn device. In certain configurations, the appendage worn device comprises at least one of an accelerometer, a location-determining sensor (e.g., GPS), a force sensor and a heart rate monitor. The unitary device may comprise a sensor configured to be placed on or within athletic apparel, such as a shoe. In yet another example, a sensor from at least two different devices is utilized to collect the data. In at least one embodiment, the device comprising a sensor utilized to capture data is also configured to provide an output of flight time. In one embodiment, the device (or another device) comprises a display device configured to display an output relating to flight time. In further embodiments, the device may comprise a communication element configured to transmit information relating to flight time to a remote device.

In another implementation, one or more attributes may be calculated from received sensor data and used as inputs to one or more walking and/or running models for predicting, among others, a speed/pace of a user. Further details of such an implementation are described in relation to block 603 of flowchart 600.

FIG. 6 is a flowchart showing an exemplary implementation of attribute calculation. In one example, this attribute calculation may be used to estimate one or more metrics associated with an activity being performed by a user, wherein this estimation may include airtime, jump height, energy expenditure, speed, and/or one or more other metrics.

Examples herein may be explained in relation to example metrics, such as airtime, however, other metrics are not excluded unless expressly written herein. In this regard, embodiments of the disclosed innovation relate to systems and methods that detect, measure, and/or report airtime in new and non-obvious ways when compared to the prior art. Previous attempts to incorporate airtime as a metric merely focused on flight of one or both feet in the context of jumps. For example, with reference to basketball players, prior attempts may have considered an offensive player making a jump shot or a defensive player attempting to jump up to block the shot of the offensive player to determine flight time. As would therefore be expected, such results would be highly correlated to total jumps during the same time period.

In accordance with various embodiments, airtime calculations are not limited to instances in which it is determined the athlete has jumped (or is jumping). Certain embodiments may calculate airtime for instances in which at least two feet are simultaneously not contacting the ground or surface. Determinations of airtime may, therefore, comprise calculating airtime for instance of side jumps/shifts (like lateral shuffling when guarding an opponent in basketball,) as well as during instances of running, jogging, sprinting, and/or similar movements. In certain embodiments, a movement (e.g., a walk) where 2 feet never simultaneously leave the ground may not be included.

In certain embodiments as generally described above, metric determinations may not be limited to calculations from two-footed jumps, in which both feet leave the surface at substantially the same time. Such jumps are often observed, for example, by basketball players while taking a shot and/or blocking a shot. In other embodiments, airtime calculations are not limited to any form of a jump, inclusive of two-footed jumps as well as one-footed jumps—in which one foot leaves the ground in advance of the other (such as, for example, when attempting a layup in a basketball game).

Further aspects of this invention relate to calculating airtime from flights of one or more feet during one or more of: running or jogging. Certain embodiments may classify the activity.

Information related to the movement of the user may be outputted as one or more data signals from one or more sensors associated with one or more sensor devices monitoring the user. In one implementation, FIG. 6 represents one or more processes carried out by at least one processor, such as processor unit 202, which may be associated with a sensor device, such as, among others, device 112, 126, 128, 130, and/or 400. In one implementation, one or more sensor devices may monitor one or more motions associated with one or more activities being performed by a user. In one embodiment, footwear, such as that shown in FIG. 3 may be utilized to capture at least a portion of the data utilized to detect when at least one foot left the ground or surface (e.g., launch), when at least one foot returned to the surface (e.g., strike) or other attributes. Various embodiments of footwear may have at least one accelerometer and/or at least one force sensor.

In some performance monitoring systems and methods, devices may not directly monitor a volume of oxygen being consumed by a user during an activity. Although oxygen consumption and/or caloric burn may be useful in some instances to measure performance or fatigue, many current systems may not accurately measure the user's performance or fatigue, e.g., due to natural variations between two athletes (including but not limited to size, weight, sex, abilities, etc.). An athlete may expend calories; however, it may not translate into adequate performance. For example, a defensive basketball player may expend a lot of calories waving their arms trying to block an offensive player, however, if they are not quick on their feet, and/or move with responsiveness, that caloric expenditure may not translate into an accurate performance metric. In one arrangement, however, received activity data may be correlated with observed oxygen consumption values for activities that may exhibit certain attributes, and associated with one or more oxygen consumption models.

One or more embodiments may receive sensor data from one or more sensors (see, e.g., block 602). In certain embodiments, the sensor data may be associated with a device worn by a user. In one example, and as previously described, said device may be, among others, device 112, 126, 128, 130, and/or 400. Accordingly, the sensor data may be received by a processor, such as processor 202 from FIG. 2, and may be received from one or more sensors described herein and/or known in the art. In one implementation, sensor data may be received at block 602 from an accelerometer located on or within footwear or otherwise at a location proximate to the athlete's foot.

In one implementation employing an accelerometer, an output of an accelerometer sensor may include an acceleration value for each of three axes (x-, y-, and z-axis). Accordingly, in one implementation, a plurality of acceleration values associated with the respective axes to which an accelerometer sensor is sensitive (x-, y-, and z-axis) may be grouped as a single acceleration data point.

In accordance with various embodiments, time stamped data (a.k.a. "timestamps" herein) may be received directly or indirectly from the sensor(s) and/or processed (e.g. block 606). Various embodiments may receive or calculate one or more timestamps or sensor attributes, such as but not limited to one or more of the following: a foot strike timestamp, a left foot strike timestamp, a right foot strike timestamp, a launch timestamp, a left foot launch time stamp, a right foot launch timestamp, derived timestamps, such as but not limited to: a left foot launch Z-axis (vertical axis with respect to the surface the user has launched from and/or the Earth's surface) derivative max timestamp, and/or a right foot launch Z-axis derivative max timestamp.

As one example, accelerometer data may be received at a frequency of, among others, 25 Hz. Additionally or alternatively, sensor data may be received from the sensor, such as accelerometer, in windows of time intervals. In one embodiment, the window (or time frame) may be about 1, 2, 3, 4 or 5 seconds in length. A window may be a period of time during which sensor data is recorded for one or more motions of a user associated with one or more activities being performed by a user. In one implementation, a sample window may include 128 samples (data points) of sensor data, wherein a sample of sensor data may include a value for each of three orthogonal axes of an accelerometer (x-axis, y-axis, and z-axis), and/or a vector normal value. In yet another implementation, sensor data received from, in one implementation, an accelerometer, may be received in windows that do not overlap and received singly, rather than simultaneously, and/or discrete from each other.

However, in alternative embodiments, those of ordinary skill will readily understand, given benefit of this disclosure, that the systems and methods described herein may be employed with any frequency of operation of an accelerometer, with a window length measuring any length of time, and using any number of samples of sensor data from within a given window. Data may be validated as it is received, such as, for example, at block 604. Data validation may include, among others, a comparison of one or more values of received sensor data to one or more threshold values, and the like. Embodiments may compare one or more strike times against launch times to filter out erroneous data. Further aspects of this disclosure relate to calculating one or more attributes from the data (see, e.g., block 606). Calculation of one or more attributes may occur before, during or after validation protocols. In one implementation, one or more attributes may be calculated for one or more of the received samples in a sample window (e.g., the 128 sample window described above). Attribute calculation may occur in real-time as the data is collected.

As discussed above, derived data, such as a launch z-axis derivative max timestamp, may be calculated. One or more calculated and/or raw attributes may be utilized to determine whether the athlete is running, jogging, conducting a sidestep, a jump, and/or performing another action—which may or may not be classified. In one embodiment, data may be used to determine whether the athlete is walking (which according to at least some embodiments would not be used in the calculation of airtime), whether a jump was initiated with a specific foot, whether the jump was a single or double-footed jump, and/or other information. In this regard, certain embodiments may compare one or more calculated attributes associated with data received from one or more sensors, and indicative of one or more activities being performed by a user, to one or more attributes associated with one or more models. In one example, one or more attributes may be utilized to calculate flight time (e.g., block 607). In this regard, although block 603 is shown below block 607 with respect to flowchart 600, certain embodiments may classify motions, such as being walking, running, jumping, etc., before determining the flight times. In this regard, block 603 may be a precursor to block 607

In accordance with one embodiment, it may be determined the relative timing of the athlete's feet leaving the surface being traversed by the athlete (launch) and/or which foot left the surface first or last since a relative time point, such as a previous last foot strike or specific foot strike. The determination may be based upon timestamps indicating the launch of each foot. Certain embodiments may determine a launch time for the last foot determined to leave the surface (a.k.a., the launch foot), as the maximum z-derivative. In various embodiments, a time stamp of the last foot to leave the ground (or have a threshold level of movement along an axis—e.g., the vertical axis) may be used as the beginning point to determine flight. Yet other embodiments may use other timestamps, such as when the first foot left the ground. For example, upon determining, such as from timestamps, that both feet were off the ground during a time frame, the first timestamp may be used to calculate airtime. In certain embodiments, the initiation point for airtime may be dependent on a type of activity, such as whether the user was running, jogging, jumping, side-stepping, etc.

In one example, one or more data points received from a sensor are aggregated into a dataset representative of one or more motions of user. Accordingly, the one or more data points may be processed to represent the data in a way that allows for one or more trends and/or metrics to be extracted from the data. In one example, acceleration data output from an accelerometer may be processed (transformed) to calculate a vector normal ("vector norm"). Additional or alternative transformations may be employed to calculate, in one example, a standard deviation of the vector normal, a derivative of the vector normal, and/or a Fast Fourier Transform (FFT) of the vector normal. Those skilled in the art will appreciate, given benefit of this disclosure, that certain transformations may combine sensor data from two or more sensors and/or with other data, such as biographical data (e.g., height, age, weight, etc.). In other embodiments, transformation may only utilize data from single sensors, such that sensor data from multiple sensors is not mixed.

In this regard, aspects of this disclosure are directed toward using one or more attributes utilized in the determination of airtime to determine other attributes. Sensor data, raw or processed may be compared to one or more models (see e.g., block 608).

Figure 7:
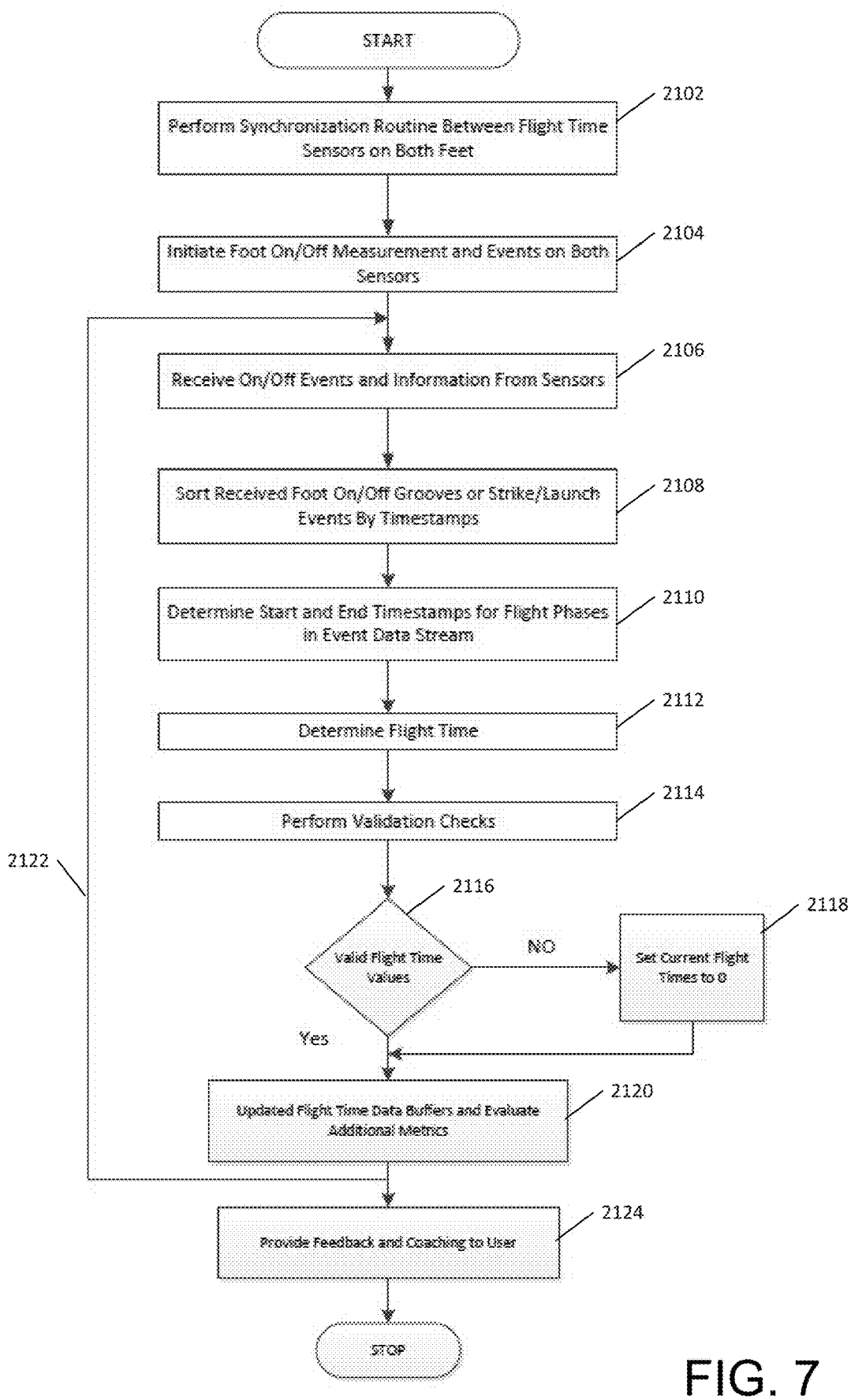
FIG. 7 shows an example flowchart that describes various features and aspects of systems and methods according to at least some examples of this invention.

In certain embodiments, total, immediate and/or average flight times may be determined. In this regard, aspects relate to measuring athletic ability or other information based upon flight time. For example, an athlete's average flight time (which may include airtime from walking and/or running) may be an indicator of athletic performance. Certain embodiments relate to determining flight time, such as the flight time during a unit of time (e.g., what is the average flight time during a minute of a game or athletic performance). For example, as shown in FIG. 7, an athlete may average 200 milliseconds per "flight" ("instantaneous flight time") in the first minute of a game and 150 milliseconds per flight another minute of the same game or performance. Flight times may be considered irrespective of "height" for example, a user may have a series of small flights during their blocking or running and thus exhibit more flight time than another player who jumped several times and/or had higher jumps.

Figure 8:
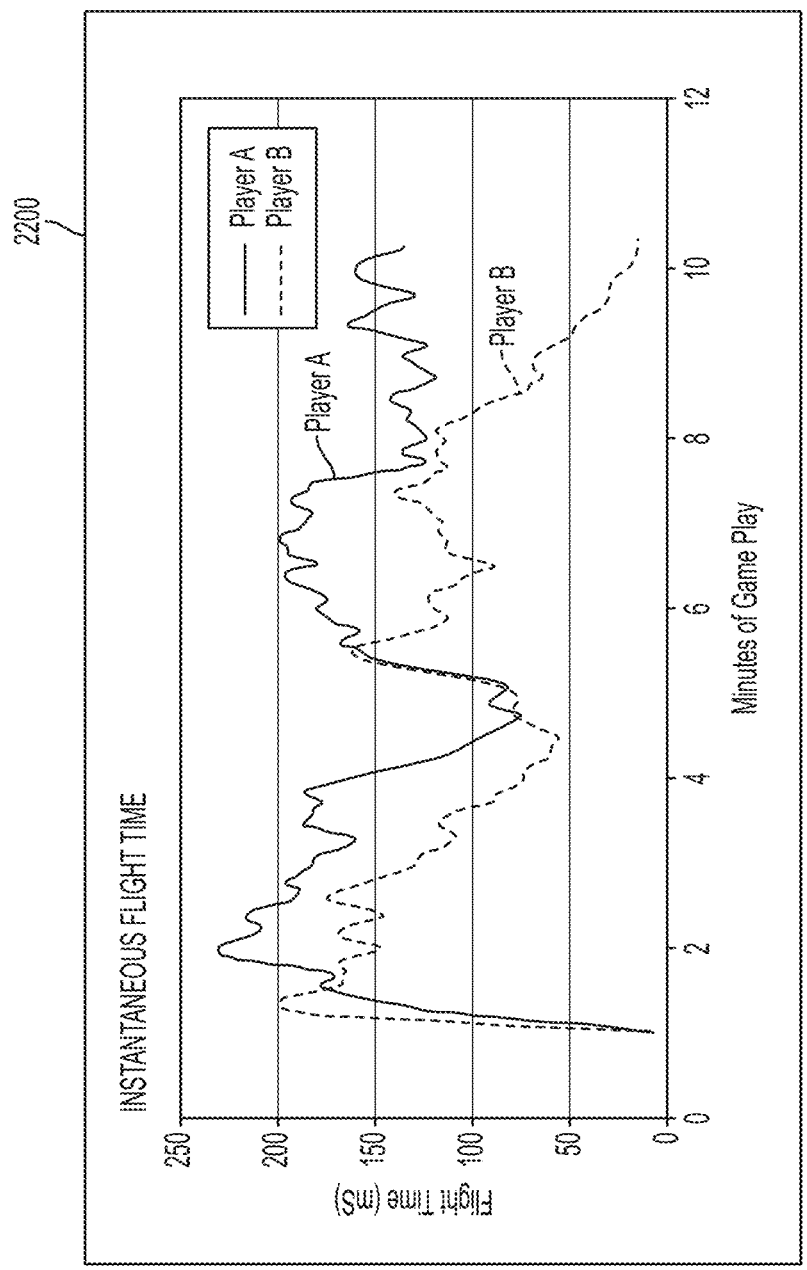
FIG. 8 shows a chart of two athlete's instantaneous flight time in accordance with one embodiment.

In another embodiment, average flight time as a function of time, such as average flight time (e.g., in milliseconds/sec) of a game or athletic performance may be determined (see, e.g., FIG. 8). For example, the average flight time (especially as more time passes during an event/game) may converge to represent the time in flight as compared with the time not in flight. Likewise, total or cumulative flight time may represent the total time in flight during a game or performance (See, e.g., FIG. 9).

Such information is an improvement over the prior art as airtime calculations according to various embodiments disclosed herein may be beneficial in training regimes. For example, a quantity of airtime within a certain time frame may be used to determine the user's level of exertion as compared to their maximum, either theoretically, a preference, or past collected data. Likewise, this information may be used to gauge one athlete's performance and/or abilities against another player's abilities, even another player performing the same position, and/or it may be used to gauge one athlete's performance at different positions (e.g., forward vs. center), as well as their "rate of fatigue." In this regard, total movements or caloric expenditure may not accurately measure the user's fatigue, ability, and/or current performance or rate of decline. In certain embodiments, force measurements, such as launch and/or strike forces may be used in conjunction with airtime determinations.

Flight time attributes may be used as inputs to one or more of, among others, models for estimation of a number of steps (during walking, which may not be considered in calculations of airtime), strides (during running), or other movements by a user, and/or models for estimation of speed and distance (pace) of a user (see e.g., block 603 of flowchart 600). Furthermore, as will be apparent from FIG. 6, one or more calculated attributes may be used as inputs to one or more models such that, in one example, a model for estimation of flight time may be executed separately from a model for calculation of airtime, a step rate, a walking speed, and/or a running speed, and the like. For example, an activity device may receive information from a user performing a basketball activity. In response, the device may process the received basketball activity data (such as, for example, block 606 of flowchart 600), and compare calculated attributes to one or more models or otherwise conduct further analysis in addition to air time. As one example, a determination to accumulate airtime, such as part of the calculations of block 607 may lead to a determination of whether a jump occurred, and if so, jump height may be determined (such as, for example, block 608). In accordance with one embodiment, determination of jump height and/or other metrics that may be related to jump height may be performed, at least in part, by comparing one or more of the data attributes used in the calculation of airtime against one or more models. As previously described, one or more models may be stored in a memory, such as memory 212, and the like, and associated with a device, including a sensor device.

Figure 10:
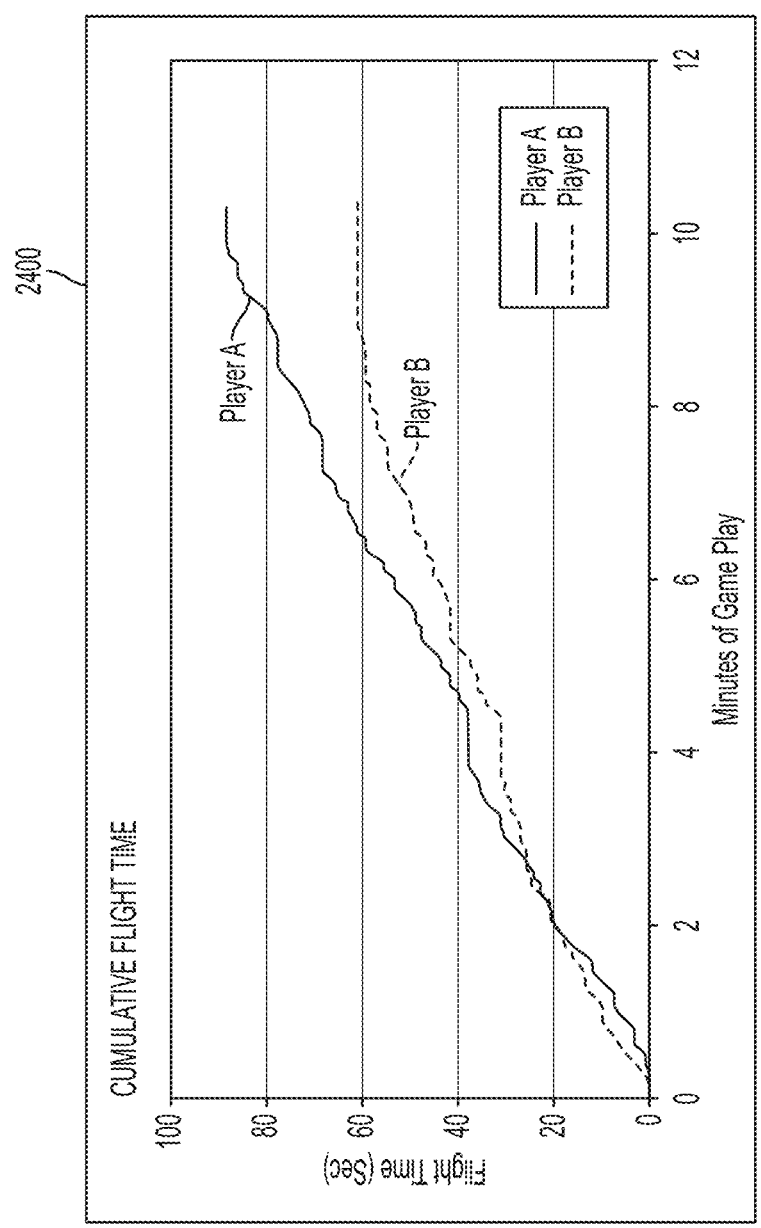
FIG. 10 shows a chart of two athlete's cumulative flight time in accordance with one embodiment.

FIG. 10 shows a flowchart of calculating jump height according to one embodiment. Flight time may be used in a linear regression to determine jump height.

As discussed above, one or more attributes calculated (including, e.g., at block 606) may be used in a determination of whether sensor data is indicative of walking, running, or another activity being performed by a user, and additionally or alternatively, the speed at which the user is walking or running, and the like. Accordingly, one or more attributes calculated at block 606 may be used as inputs to block 603. In particular, one or more attributes may be communicated from block 606 to decision block 616. At block 616, one or more processes may be executed to determine whether a user is running or walking, or performing another activity. If it is determined that a user is performing an activity other than running or walking, the process proceeds from block 616 to 618, at which no speed is defined. Accordingly, for a user performing activity other than running or walking, no processes are executed to define the speed at which the user is traveling, and the like. If it is determined, at decision 616, that's the user is running or walking, decision 620 may be implemented to determine whether the activity is walking or running. Example embodiments for selecting an activity, such as running or walking, are provided herein. In one embodiment, if it is determined that a user is running, one or more attributes may be communicated to a running model, such as to determine speed (e.g., see block 622). If, however, it is determined that a user is walking, certain embodiments may communicate one or more attributes to a walking model, such as to determined speed (e.g., block 624). Results from data processing by these models may be used, e.g., at steps 607, 608.

A more detailed description of FIGS. 7-11 and potential features thereof is provided below.

As described above, aspects of this invention can be used to determine "flight time." FIG. 7 includes a flowchart describing one such example system and method.

The process of FIG. 7 starts with a data set that includes data collected, e.g., from footwear based sensors, including at least some right foot launch, right foot strike, left foot launch, and left foot strike data (e.g., collected from one or more sensors provided in an article of footwear, such as force or accelerometer based sensor data, like that described in conjunction with FIG. 3). In Step 2102, this example system and method may synchronize the sensor events registered by the two shoe based sensor systems, if necessary, e.g., to account for deviations in sensor clocks and/or transmission times. In particular arrangements, the systems and methods may measure the required transmission time between each of the sensors and the activity processing system and subsequently use the measured transmission time to adjust a time associated with each of the detected sensor events. Additionally or alternatively, synchronization may include temporally sorting the events received. In some examples, the foot strike and foot launch event data might not be received in an order in which the events were detected. Accordingly, the system and method may preprocess the event data to order the events according to the time at which they were detected. As another potential feature (in addition to or in place of any of those described above), as use of the system and method begin (e.g., when a "start" button or function is initiated, when the player registers to go into the game, etc.), at Step 2102 the clocks in and/or associated with each shoe may be synchronized to the same time (e.g., a "0" starting time).

Once the sensors synchronized and/or otherwise are ready to go, at Step 2104, the system and method may initiate measurements and registration of events by the sensors in each shoe (e.g., initiate determination of "foot strike" or "foot on" events and initiate determination of "foot launch" or "foot off" events), and this "foot strike/foot launch" data is received at Step 2106.

As or after the foot strike/foot launch data is received, at Step 2108, the data may be sorted based on the time it was generated (e.g., based on the "timestamps" associated with and included in the data for each foot strike and foot launch event). Therefore, incoming data from the shoe based sensors may include one of more the following types of information: (a) identification of the sensor generating the data (e.g., right shoe, left shoe, a particular sensor on the shoe (if multiple sensors are present), etc.), (b) timestamp information (e.g., when the data was measured), (c) type of event (e.g., launch or strike), (d) other data associated with the measurement (e.g., landing force, landing acceleration, launch acceleration, etc.), etc. Based on the information contained in the data stream, in Step 2110, the "start" and "end" timestamps for "flight times" (e.g., corresponding pairs of consecutive "Foot A launch" and "Foot B strike" events and pairs of consecutive "Foot B launch" and "Foot A strike" events, pairs of "Foot A strike" and "Foot A launch" events, pairs of "Foot B strike" and "Foot B launch" events, etc.). These start and end timestamps for the consecutive pairs of launch and strike events may be used to determine "flight time" associated with the flight events at Step 2112.

Once flight times for each desired flight event are determined, validation checks can be performed at Steps 2114-2118 to determine/confirm whether the "flight" data represents a legitimate jump and/or if desired, "flight time" associated with running, jogging, sprinting, or the like. As some more specific examples, one potential validation check may be determining whether the determined "flight time" (from the event timestamps) is longer than humanly possible to constitute flight from an actual "jump" or "run" activity. For example, if the timestamp data stream indicates that the player has been up in the air for several seconds, this "flight time" might be determined to not constitute a jump or jump (e.g., answer "no" at Step 2116), in which case, the "flight time" for that pair of foot launch and foot strike events may be set to 0 (Step 2118).

A long flight time, however, does not necessarily compel a determination that the data is faulty and/or that the noted activity did not constitute a "jump" or true "flight time" (optionally including "flight time" associated with running, jogging, and/or sprinting activities). Rather, systems and methods according to at least some examples of this invention may further analyze data that indicates that an excessively long "flight time" occurred (or optionally all flight time data). For example, in some instances when playing basketball, a player might prolong a "flight time" by grasping and holding onto the rim or net and/or by not landing on his/her feet (e.g., landing on one's back, knees, elbows, etc.). Therefore, rather than automatically throwing out data indicating a flight time longer than a predetermined threshold value, data and/or information from other sensors and/or sources could be consulted to see if a more accurate picture can be developed of what happened during the long flight time in question. For example, if the player grabbed onto the rim, the foot and/or body based sensors may register the initial lift off, a "hanging" in mid-air phase (when the rim or net is grabbed) or even a second lift phase (if the player pulls himself further upward using the rim/net), followed by a downward movement phase. As another option, a wrist borne sensor may be used to detect prolonged close proximity to the rim during a time when both feet are off the ground. Video data also may be consulted to determine whether a specific flight event is legitimate or fully legitimate. If such legitimate flight events are detected or determined, then at Step 2118, rather than setting the flight time to 0 for that event, the flight time could be adjusted, e.g., to count "flight time" only as the "up" and "down" time associated with that jump or other flight event (and to not add in the additional time when the player swung from the rim or net, further propelled himself/herself upward using the rim or net, etc. as part of the flight time for that event).

In an event where the player lands off his feet, a body based sensor (or an accelerometer included with the shoe based sensors) may detect an abrupt change in velocity and/or acceleration when the player lands on the floor. If such events are detected, then at Step 2118, rather than setting the flight event time to 0 for that event, the time could be adjusted, e.g., to count "flight time" as the time between the last "foot launch" event and the following on-floor landing event by a body part other than a foot.

Once the flight times are determined as valid (answer "yes" in Step 2116), determined as invalid and set to 0 (Step 2118), and/or adjusted (in the alternatives for Step 2118 discussed above), at Step 2120, the data in the flight time buffer memory can be updated (e.g., with updated determinations of average flight time or cumulative/total flight time, etc.) and/or other desired data may be generated and/or other metrics may be determined. If more data remains available for evaluation, the system and method can loop back (loop 2122) to Step 2106 and analyze the next timestamp data set and/or any available additional data. At any desired or appropriate time in the process (e.g., including before loop 2122 occurs), flight time data and/or other feedback, metrics, and/or information can be made available to the player, the coach, and/or any other designated party (Step 2124). Additionally or alternatively, at Step 2124, coaching and/or training information may be presented to the user, e.g., in the form of workout plans, workout drills, playing tips or advice, etc.

Figure 9:
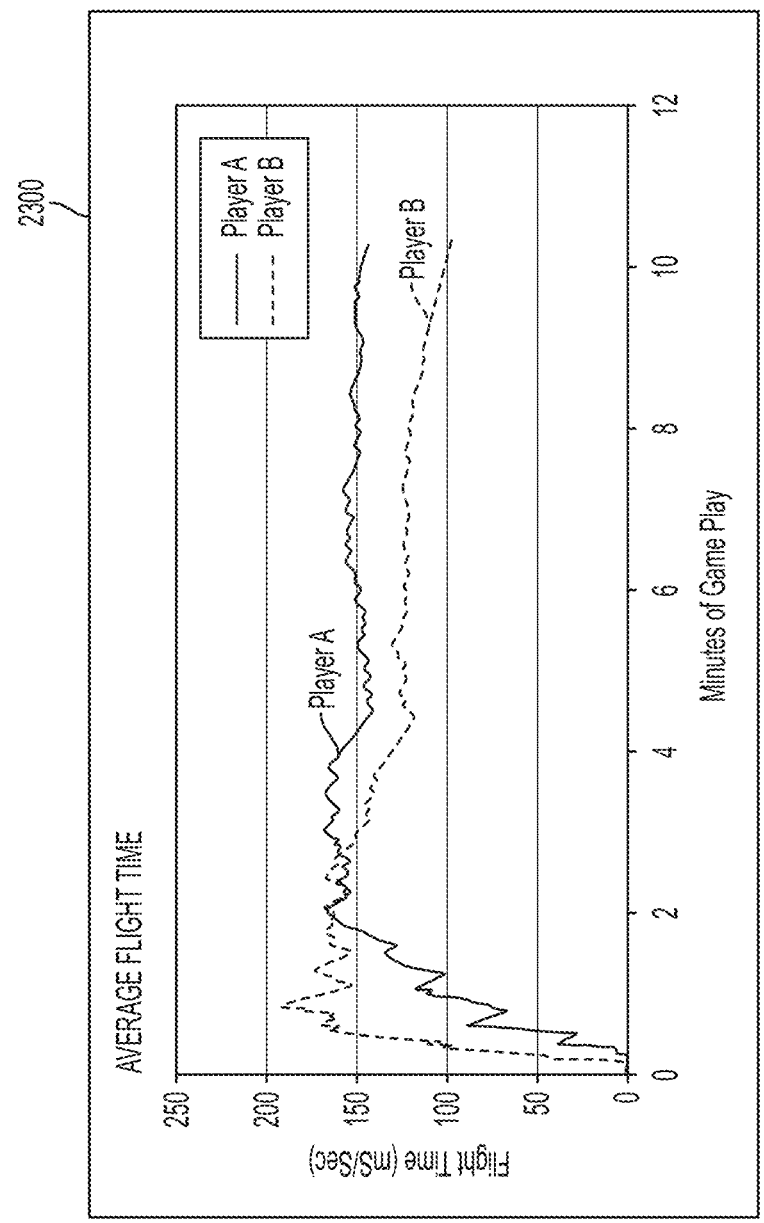
FIG. 9 shows chart of two athlete's average flight time in accordance with one embodiment.

Information relating to "flight time" and/or any desired parameters and/or metrics may be provided to the user in a variety of ways, including the various ways described above. FIGS. 8-10 provide some example displays and/or user interfaces (e.g., for display screens on computers, smart phones, etc.) that may provide feedback and/or information to users in accordance with at least some examples of this invention. As described above, values associated with a determination of "flight time" for individual flight events (e.g., time between consecutive foot landing and prior foot launch events) may be added together (e.g., in a flight time buffer memory) or the buffer may otherwise be updated based upon the measured/detected flight times (e.g., blocks 1050*b*, 1180, 2120). This data may be used in various ways.

For example, as shown in FIG. 8, one user interface screen 2200 may illustrate one or more players' "instantaneous flight time" (in milliseconds), per flight, over the course of his/her playing time in the game (minutes of game play). In the example of FIG. 8, the performances of two players are shown overlapping to enable comparison of their performances (these performances do not need to have taken place at the same time, in the same game, and/or at the same location). In the illustrated example of FIG. 8, it can be seen that while both Player's instantaneous performances (e.g., average flight time per flight) followed similar trends, particularly at a start, Player B's flight time performance, however, tailed off dramatically at the end as compared to Player A's performance (e.g., after about 8 minutes of playing time).

FIG. 9 illustrates an example user interface screen 2300 that shows one or more players' "average flight time" (in milliseconds/second) over the course of his/her playing time in the game (minutes of game play). In the example of FIG. 9, the performances of two players again are shown overlapping to enable comparison of their performances (again, these performances do not need to have taken place at the same time, in the same game, and/or at the same location). In the illustrated example of FIG. 9, it can be seen that while Player B's average flight time was a little higher than Player A when his/her play started (e.g., inside the first two minutes), Player A maintained a higher flight time over the full course of his/her play. The "average flight time" (especially as more time passes during an event/game) may converge or flatten out (as shown in FIG. 9) and may be considered as a representation of a player's "time in flight" as compared with the time not in flight (e.g., time spent running or jumping as compared to time not running or jumping).

FIG. 10 shows an example user interface screen 2400 that provides another interesting metric and information in accordance with at least some examples of this invention. More specifically, FIG. 10 shows "cumulative flight time" (in seconds) for one or more individual players over the course of their playing time in the game. In this illustrated example, Player A shows a relatively constant, steady accumulation of "flight time" over the course of his/her playing time whereas Player B's performance curtailed off more quickly and resulted in substantially less overall flight time.

These metrics and comparisons (e.g., from FIGS. 8-10) provide valuable information to the player or coach as they compare players, compare player fitness/performance levels, compare individual player performance changes over time (e.g., the Player A and Player B curves may represent one player's performance at different times) and/or develop training and practice sessions for the player(s). Additionally or alternatively, if desired, players could allow others to view their "flight time" data and use this information (e.g., in social networks) to create groups of friends, challenges, and/or other games and activities that will tend to motivate players to compete, strive to get better, and play harder. These types of interactions, comparisons, and challenges with others also can help set goals and/or avoid boredom.

Figure 11:
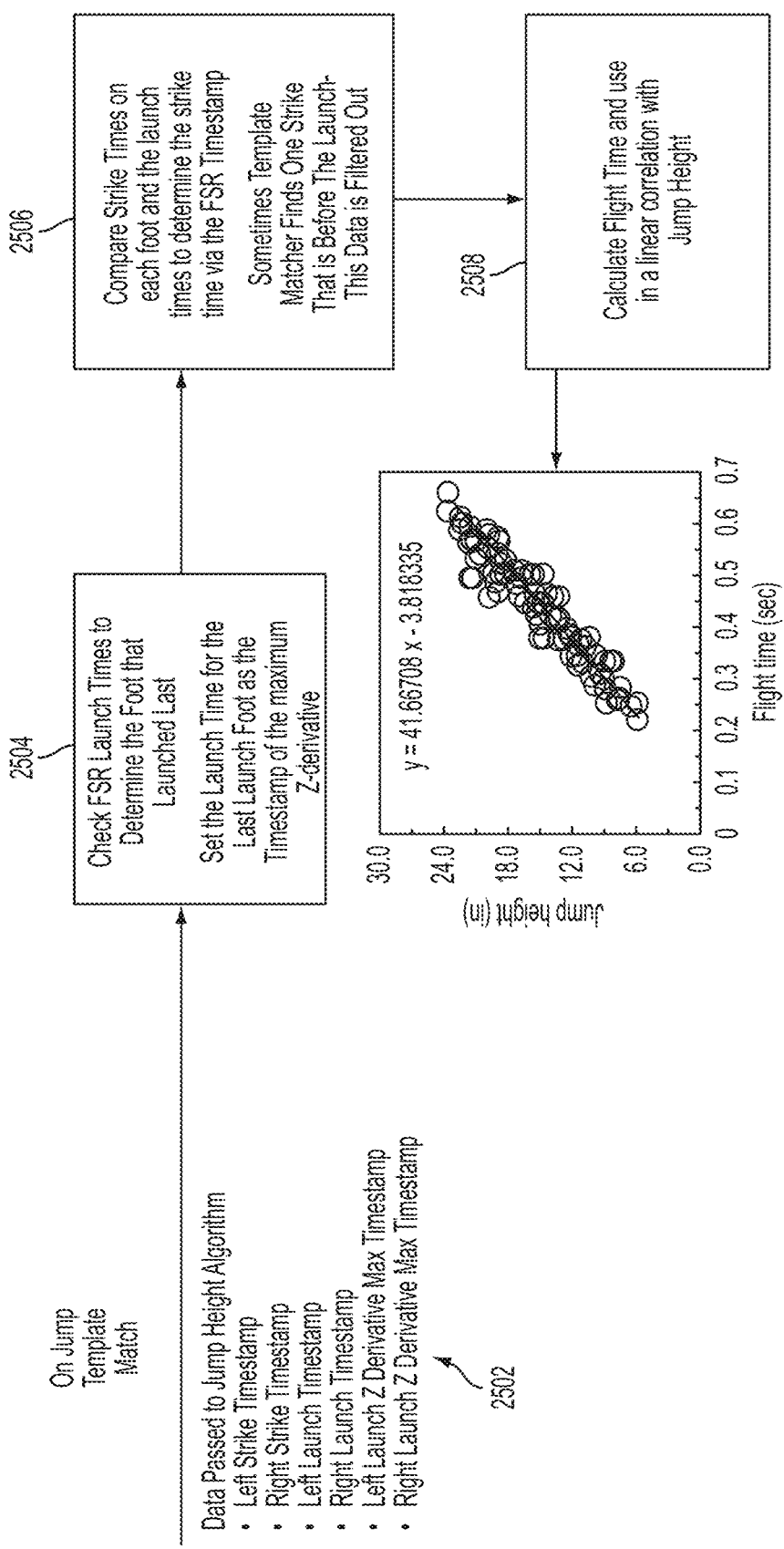
FIG. 11 shows a flowchart that may be implemented to determine jump height in accordance with one embodiment.

Other metrics and options are possible without departing from this invention. For example, as shown in FIG. 11, systems and methods according to at least some examples of this invention may create, determine, and maintain a jump "height" metric for players. More specifically, FIG. 11 describes information that may be utilized in a "Jump Height" determining algorithm to determine "jump height" associated with any desired "flight time" event. As shown, the jump height algorithm may take as input data 2502 one or more of: left foot strike timestamp; right foot strike timestamp; left foot launch timestamp; right foot launch timestamp; left foot launch data in the Z (vertical) direction (e.g., Z derivative max, to get upwardly directed force information); and right foot launch data in the Z (vertical) direction (e.g., Z derivative max, to get upwardly directed force information). At Step 2504, the foot sensor data is reviewed to determine the last foot to launch so that both feet are indicated as being up in the air, and the timestamp associated with that foot's launch is used as the timestamp of the maximum Z-derivative for that foot and that event. Then, at Step 2506, the strike times for each foot are compared to the launch times for each foot to determine the overall strike time (when the first foot strike occurs). If it is determined that either foot strike event occurs before the last foot launched, the data is filtered out (and no "jump height" is determined based on that data set). Once valid "flight event" data is determined (e.g., the time between the last foot launch time, with both feet in the art, and the first foot strike time) for a data set, the "jump height" for that data set is determined based on the flight time (Step 2508). While any desired algorithm may be used for determining jump height from flight time, in this illustrated example jump height is calculated based on the following equation:

$$y=41.66708x-3.818335 \quad \text{(Eq. 1)},$$

wherein "y" represents jump height in inches and "x" represents flight time in seconds. This equation was derived from a linear regression of measured jump height and flight time data.

Players could challenge themselves and/or one another to attain specific "jump height goals," e.g., based on a cumulative jump height for multiple "flight events" determined by systems and methods according to this invention (e.g., first to "jump over" the Eiffel Tower, etc.). Other "jump height" metrics also may be used in challenges of this type, including an "instantaneous jump height," "average jump height," etc.

If desired, systems and methods according to at least some examples of this invention may define the various metrics more granularly than simply determining various flight time features. As noted above, using different sensors and/or combinations of sensor input data, different types of "flights" can be determined and distinguished from one another, including walking v. jogging v. running v. sprinting v. jumps (and/or v. running jumps v. vertical jumps). Therefore, if desired, "flight time" metrics (including instantaneous, average, or cumulative/total flight time) and/or jump height metrics (including instantaneous, average, or cumulative/total jump height) as described above in conjunction with FIGS. 8-11 can be further broken down into flight times and/or jump heights associated with any one or more of these different types of activities (or any desired combination of these activities), including one or more of: walking time; jogging time; running time; sprinting time; jumping time; running jump time; vertical jump time; jogging flight time; running flight time; sprinting flight time; jump flight time; vertical jump flight time; running jump flight time; jogging jump height; running jump height; sprinting jump height; jumping jump height; vertical jumping jump height; and running jump type jump height.

Other ways of providing more detailed feedback and data to the user are possible without departing from this invention. For example, by combining the flight time and jump data (and optionally the more granular flight time and jump data described above) with other input data, systems and methods according to at least some examples of this invention may further provide individual "flight time" and "jump height" metrics for players on offense and on defense (e.g., "offensive flight time" and "defensive flight time"). As some more specific examples, sensor data (e.g., GPS sensors, image sensors, proximity sensors, etc.) could be used to provide data to systems and methods according to some examples of the invention where play is occurring on the floor so that a determination can be made as to whether the player is on the offensive or defensive side of the floor. Abrupt changes in acceleration, velocity, and/or movement values and/or directions by multiple players also could be considered an indicator of a change in ball possession (transitioning the players from offense to defense and vice versa). "Ball possession" determination systems and methods also may be used to determine whether an individual player and/or team is on offense or defense. Some example "ball possession" determination systems and methods are described, for example, in U.S. Patent Appln. Publn. No. 2010/0184564 A1 published Jul. 22, 2010, which publication is entirely incorporated herein by reference for all non-limiting purposes.

With such "offense" or "defense" input, systems and methods according to at least some examples of this invention may break down the flight times and/or jump heights to include one or more of: offense walking, jogging, running, sprinting, jumping, running jump, and/or vertical jump times; offense jogging flight time; offense running flight time; offense sprinting flight time; offense jump flight time; offense vertical jump flight time; offense running jump flight time; offense jogging jump height; offense running jump height; offense sprinting jump height; offense jumping jump height; offense vertical jumping jump height; offense running jump type jump height; defense walking, jogging, running, sprinting, jumping, running jump, and/or vertical jump times; defense jogging flight time; defense running flight time; defense sprinting flight time; defense jump flight time; defense vertical jump flight time; defense running jump flight time; defense jogging jump height; defense running jump height; defense sprinting jump height; defense jumping jump height; defense vertical jumping jump height; and/or defense running jump type jump height.

Jump detection and/or jump determination information in accordance with at least some examples of this invention also may be used to provide additional useful information, particularly if combined with information regarding results of the jumping action. For example, determination that: (a) a player has possession of the ball (e.g., using a wrist based or body based ball contact/proximity sensing system), (b) the player in possession of the ball jumps vertically or jumps while running (e.g., using footwear based sensors), and (c) the player releases possession of the ball can be used by systems and methods according to examples of this invention as a determination that the player: (i) took a shot (e.g., if ball proximity to the rim and/or backboard is determined, and optionally whether the player made or missed the shot), (ii) made a pass (e.g., if ball possession by another player on the same team is determined), (iii) made a turnover (e.g., if ball possession by another player on the other team is determined), or (iv) had the shot or pass blocked (e.g., if an opposing player contacts the ball and changes its trajectory). As another example, determination that a player not in possession of the ball (but optionally detected as being in proximity to the ball): (a) jumps (e.g., using footwear based sensor) and (b) contacts the ball (e.g., with a ball based sensor) to change the trajectory of the ball may be used to determine that the player blocked another player's shot and/or intercepted a pass. An yet another example, determination that a player not in possession of the ball (but optionally detected as being in proximity to the ball): (a) jumps (e.g., using footwear based sensor), (b) possesses the ball (e.g., with a ball based sensor), and (c) lands the jump (before or after gaining possession of the ball) may be used to determine that the player rebounded the ball or caught a pass (from a teammate or from one of the other team's players). Flight times and/or jump heights associated with any of these other detected activities could be tallied and the information presented to the player, coach, etc. as useful coaching/training data and/or metrics.

CONCLUSION

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of this disclosure will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

We claim:

1. A method comprising:
receiving, from a first sensor system, launch input data indicating a plurality of foot launch events during a first time period;
receiving, from the first sensor system, strike input data indicating a plurality of foot strike events during the first time period;
determining, by a computing device and based on the launch input data and the strike input data, a first activity type for an athletic performance of a user during the first time period;
determining, based on the determined first activity type, a first flight time associated with the athletic performance of the user during the first time period;
determining, by the computing device, that the first flight time exceeds a threshold value;
based on the determining that the first flight time exceeds the threshold value, receiving, from a second sensor system, first input data associated with the athletic performance; and
using the first flight time and the first input data to determine a corrected flight time associated with the athletic performance.

2. The method of claim 1, wherein the determining the first activity type further comprises:
determining at least one of:
a particular foot used to initiate the athletic performance, or
a number of feet used to initiate the athletic performance.

3. The method of claim 1, wherein the determining the first activity type further comprises:
comparing a first set of attributes for at least one of the launch input data or the strike input data with a second set of attributes for one or more activity estimation models.

4. The method of claim 1, wherein the determining the first flight time further comprises:
determining based on a foot of the user satisfying a threshold level of movement along a vertical axis, an initiation point for the first flight time.

5. The method of claim 1, wherein the determining the first flight time further comprises:
determining an initiation point for the first flight time based on the determined first activity type.

6. The method of claim 1, further comprising:
comparing a first set of timestamps associated with the launch input data and a second set of timestamps associated with the strike input data; and
discarding, based on the comparing, one or more of:
the plurality of foot launch events; or
the plurality of foot strike events.

7. The method of claim 1, wherein the corrected flight time comprises a portion of the first flight time.

8. The method of claim 1, further comprising:
receiving, from the second sensor system, possession data indicating whether the user is within a threshold proximity to an object; and
determining, based on the possession data and the first flight time, that the user performed a predetermined activity as part of the athletic performance.

9. The method of claim 1, wherein the first input data comprises sensor data indicating a change in acceleration or velocity of the user.

10. The method of claim 1, further comprising:
determining transmission times associated with one or more sensors of the first sensor system; and
adjusting, based on the determined transmission times, a set of timestamps associated with at least one of the launch input data or the strike input data.

11. The method of claim 1, wherein the using the first flight time and the first input data to determine the corrected flight time further comprises:
determining, based on the first input data, a suspension time associated with the athletic performance;
determining, based on the first flight time and the suspension time, a first time duration; and
based on the first time duration being less than a predetermined value, determining the corrected flight time.

12. An apparatus for analyzing an athletic performance, comprising:
one or more processors;
memory storing computer executable instructions that, when executed by the one or more processors, cause the apparatus to:

receive, from a first sensor system, launch input data indicating a plurality of foot launch events during a first time period;
receive, from the first sensor system, strike input data indicating a plurality of foot strike events during the first time period;
determine, based on the launch input data and the strike input data, a first activity type for an athletic performance of a user during the first time period;
determine, based on the determined first activity type, a first flight time associated with the athletic performance of the user during the first time period;
determining that the first flight time exceeds a threshold value;
based on the determining that the first flight time exceeds the threshold value, receive, from a second sensor system, first input data associated with the athletic performance; and
use the first flight time and the first input data to determine a corrected flight time associated with the athletic performance.

13. The apparatus of claim 12, wherein the instructions, when executed, further cause the apparatus to determine the first activity type by:
determining at least one of:
a particular foot used to initiate the athletic performance, or
a number of feet used to initiate the athletic performance.

14. The apparatus of claim 12, wherein the instructions, when executed, further cause the apparatus to determine the first activity type by:
comparing a first set of attributes for at least one of the launch input data or the strike input data with a second set of attributes for one or more activity estimation models.

15. The apparatus of claim 12, wherein the instructions, when executed, further cause the apparatus to determine the first flight time by:
determining based on a foot of the user satisfying a threshold level of movement along a vertical axis, an initiation point for the first flight time.

16. The apparatus of claim 12, wherein the instructions, when executed, further cause the apparatus to determine the first flight time by:
determining an initiation point for the first flight time based on the determined first activity type.

17. The apparatus of claim 12, wherein the instructions, when executed, further cause the apparatus to:
compare a first set of timestamps associated with the launch input data and a second set of timestamps associated with the strike input data; and
discard, based on the comparing, one or more of the plurality of foot launch events.

18. The apparatus of claim 12, wherein the corrected flight time comprises a portion of the first flight time.

19. The apparatus of claim 12, wherein the instructions, when executed, further cause the apparatus to:
receive, from the second sensor system, possession data indicating whether the user is within a threshold proximity to an object; and
determine, based on the possession data and the first flight time, that the user performed a predetermined activity as part of the athletic performance.

20. One or more non-transitory computer readable media storing instructions that, when executed cause:
receiving, from a first sensor system, launch input data indicating a plurality of foot launch events during a first time period;
receiving, from the first sensor system, strike input data indicating a plurality of foot strike events during the first time period;
determining, based on the launch input data and the strike input data, a first activity type for an athletic performance of a user during the first time period;
determining, based on the determined first activity type, a first flight time associated with the athletic performance of the user during the first time period;
determining that the first flight time exceeds a threshold value;
based on the determining that the first flight time exceeds the threshold value, receiving, from a second sensor system, first input data associated with the athletic performance; and
using the first flight time and the first input data to determine a corrected flight time associated with the athletic performance.

21. The one or more non-transitory computer readable media of claim 20, wherein the instructions, when executed, cause determining the first activity type by further causing:
determining at least one of:
a particular foot used to initiate the athletic performance, or
a number of feet used to initiate the athletic performance.

22. The one or more non-transitory computer readable media of claim 20, wherein the instructions, when executed, cause determining the first activity type by further causing:
comparing a first set of attributes for at least one of the launch input data or the strike input data with a second set of attributes for one or more activity estimation models.

23. The one or more non-transitory computer readable media of claim 20, wherein the instructions, when executed, cause determining the first flight time by further causing:
determining an initiation point for the first flight time based on the determined first activity type.

* * * * *